US008795250B2

(12) United States Patent
O'Connell

(10) Patent No.: US 8,795,250 B2
(45) Date of Patent: Aug. 5, 2014

(54) ABSORBENT ARTICLE HAVING LEG CUFFS

(75) Inventor: Susan O'Connell, State College, PA (US)

(73) Assignee: First Quality Baby Products, LLC, Great Neck, NY (US)

( * ) Notice: Subject to any disclaimer, the term of this patent is extended or adjusted under 35 U.S.C. 154(b) by 150 days.

(21) Appl. No.: 12/749,697

(22) Filed: Mar. 30, 2010

(65) Prior Publication Data
US 2011/0245792 A1 Oct. 6, 2011

(51) Int. Cl.
*A61F 13/15* (2006.01)
(52) U.S. Cl.
USPC ............ 604/385.25; 604/385.27; 604/385.28; 604/385.24
(58) Field of Classification Search
USPC .............. 604/385.25, 385.27, 385.28, 385.24
See application file for complete search history.

(56) References Cited

U.S. PATENT DOCUMENTS

| | | |
|---|---|---|
| 4,695,278 A | 9/1987 | Lawson |
| 5,582,600 A | 12/1996 | Loh |
| 5,601,546 A | 2/1997 | Tanji et al. |
| 5,624,426 A | 4/1997 | Roe et al. |
| 5,776,121 A | 7/1998 | Roe et al. |
| 5,911,713 A | 6/1999 | Yamada et al. |
| 5,993,433 A | 11/1999 | St. Louis et al. |
| 6,045,545 A | 4/2000 | Vandemoortele et al. |
| 6,102,892 A | 8/2000 | Putzer et al. |
| 6,440,117 B1 | 8/2002 | Itoh et al. |
| 6,547,773 B2 | 4/2003 | Kleinschmidt et al. |
| 6,569,140 B1 | 5/2003 | Mizutani et al. |
| 6,613,033 B1 | 9/2003 | Popp et al. |
| 7,160,282 B2 | 1/2007 | Sayama |
| 7,435,243 B2 | 10/2008 | Miyamoto |
| 7,527,616 B2 | 5/2009 | Miyamoto |
| 7,572,248 B2 | 8/2009 | Ashton et al. |
| 7,618,404 B2 | 11/2009 | LaVon et al. |
| 8,613,737 B2 | 12/2013 | Miyamoto |
| 2004/0127882 A1 | 7/2004 | Weber |
| 2005/0234411 A1 | 10/2005 | Ashton et al. |
| 2006/0041240 A1 | 2/2006 | Erdman |
| 2007/0088309 A1 | 4/2007 | Ehrnsperger et al. |
| 2009/0247975 A1 | 10/2009 | LaVon et al. |

OTHER PUBLICATIONS

International Search Report of PCT/US 2011/030547, dated Jun. 7, 2011.
Written Opinion of the International Searching Authority of PCT/US 2011/030546, dated Jun. 7, 2011.

*Primary Examiner* — Jacqueline F. Stephens
(74) *Attorney, Agent, or Firm* — Amster, Rothstein & Ebenstein LLP

(57) ABSTRACT

An absorbent article comprises a chassis having a front waist portion, a back waist portion, and a crotch portion extending between the front and back waist portions. The chassis includes a liquid pervious topsheet, a liquid impervious backsheet, and an absorbent core disposed between the topsheet and the backsheet. An outer leg cuff is disposed outward of each of the longitudinal side edges of the chassis having elastics forming a gather along at least a portion thereof. One or more inner leg cuffs are disposed on the inside surface of the chassis along each of the longitudinal side edges thereof having elastics forming a gather along at least a portion of the crotch portion. One or more fastening components are disposed at the outer longitudinal side of the outer leg cuffs to fasten the absorbent article around the waist of the wearer.

23 Claims, 4 Drawing Sheets

ABSORBENT ARTICLE HAVING LEG CUFFS

FIELD OF THE INVENTION

The present invention relates generally to disposable absorbent articles such as disposable diapers, and more specifically to absorbent articles having leg cuffs.

BACKGROUND OF THE INVENTION

Infants and other incontinent individuals wear disposable absorbent articles such as diapers to absorb and contain body exudates discharged from the body. Absorbent articles function to contain the discharged materials in isolation from the body of the wearer on one side, and from the wearer's garments and/or bedding on the other. Absorbent articles are typically constructed from a combination of liquid and vapor pervious and impervious materials which respectively allow the passage of liquid into the diaper and prevent its exit therefrom.

While many developments have been made in the art of absorbent articles, further improvements in at least one of improved fit, comfort, efficient manufacturing, and visual appearance are needed.

SUMMARY OF THE INVENTION

According to an example embodiment of the present invention, an absorbent article has an inside surface that faces a wearer's body when the absorbent article is worn, and an outside surface opposite the inside surface. The absorbent article comprises a chassis having a front waist portion, a back waist portion, and a crotch portion extending between the front and back waist portions, and having longitudinal side edges and lateral side edges. The chassis includes a liquid pervious topsheet, a backsheet of which at least a portion is liquid impervious, and an absorbent core disposed between the topsheet and the backsheet. An outer leg cuff is disposed outward of each of the longitudinal side edges of the chassis, each of the outer leg cuffs having an inner longitudinal side edge attached along at least a portion of one of the longitudinal sides of the chassis and an outer longitudinal side edge having elastics forming a gather along at least a portion thereof. One or more inner leg cuffs are disposed on the inside surface of the chassis along each of the longitudinal side edges thereof, each of the inner leg cuffs having a proximal longitudinal side edge attached along the outer longitudinal side edge of one of the outer leg cuffs and a distal longitudinal side edge having elastics forming a gather along at least a portion of the crotch portion. One or more fastening components are disposed at the outer longitudinal side of the outer leg cuffs to fasten the absorbent article around the waist of the wearer.

In at least one embodiment, at least a portion of the distal longitudinal side edge of each of the inner leg cuffs is unattached so as to be spaced apart from the inside surface of the chassis.

In at least one embodiment, each of the inner leg cuffs are attached to at least one of the outer leg cuff and the topsheet moving inward from the proximal longitudinal side edge toward the distal longitudinal side edge of the inner leg cuff.

In at least one embodiment, each of the inner leg cuffs are attached at the distal longitudinal side edge thereof to at least one of the outer leg cuff and the topsheet adjacent at least one of the front and back waist portions.

In at least one embodiment, the elastics are disposed adjacent the terminal, longitudinal side edges of the outer leg cuffs.

In at least one embodiment, a portion of the outer leg cuff is disposed outward of the elastics and is folded over to enclose the elastics within a fold of the leg cuff along the terminal, longitudinal side edge thereof.

In at least one embodiment, the inner and outer leg cuffs are joined to the chassis by attachment to topsheet, the backsheet, or between the topsheet and backsheet.

In at least one embodiment, the inner and outer leg cuffs are comprised of at least one of a nonwoven, a film, and a laminate thereof.

In at least one embodiment, at least one of the inner and outer leg cuffs are comprised of a material which is substantially non-elastic.

In at least one embodiment, at least one of the inner and outer leg cuffs are comprised of a material that is breathable to at least one of air and water vapor.

In at least one embodiment, at least one of the inner and outer leg cuffs are comprised of a material which is substantially elastic in cross-direction (CD).

In at least one embodiment, the fastening components comprise: a first side back panel and a second side back panel extending outward from the outer leg cuffs adjacent the back waist portion; and a fastener disposed at the outside edge of each of the first side back panel and second side back panel adapted for attachment to the front waist portion of the chassis.

In at least one embodiment, the first and second side back panels are attached between the outer leg cuffs and the inner leg cuffs.

In at least one embodiment, the first and second back side panels are comprised of at least one of a nonwoven, a film, and a laminate thereof.

In at least one embodiment, the first and second back side panels are comprised of a substantially non-elastic material.

In at least one embodiment, the first and second back side panels are comprised of a substantially elastic material.

In at least one embodiment, the fasteners are adapted for attachment to the outside surface of the front waist portion of the chassis.

In at least one embodiment, the fasteners are adapted for attachment to landing zones on the outside surface of the front waist portion of the chassis.

In at least one embodiment, the absorbent article further comprises: a first side front panel and a second side front panel extending outward from the outer leg cuffs adjacent the front waist portion.

In at least one embodiment, the first and second side front panels are attached between the outer leg cuff and the inner leg cuff.

In at least one embodiment, the fasteners are adapted for attachment to an outside surface of the front side panels.

In at least one embodiment, the topsheet is comprised of a nonwoven material.

In at least one embodiment, the backsheet is comprised of a film, a nonwoven, or a laminate thereof.

Other features and advantages of the present invention will become readily apparent from the following detailed description, the accompanying drawings and the appended claims.

BRIEF DESCRIPTION OF THE DRAWINGS

The above and related objects, features and advantages of the present invention will be more fully understood by reference to the following, detailed description of the example embodiments of the present invention when taken in conjunction with the accompanying figures.

DESCRIPTION OF THE PREFERRED EMBODIMENTS

As used herein, the term "absorbent article" refers to devices which absorb and contain body exudates, and more specifically, refers to devices which are placed against or in proximity to the body of the wearer to absorb and contain the various exudates discharged by the body. The term "disposable" is used herein to describe absorbent articles which are not intended to be laundered or otherwise restored or reused as an absorbent article, but instead are intended to be discarded after a single use and, preferably, to be recycled, composted or otherwise disposed of in an environmentally compatible manner. The term "proximal" is used herein to describe a feature that is located closer to the absorbent article, while the term "distal" is used herein to further away from the absorbent article.

Figure 1:
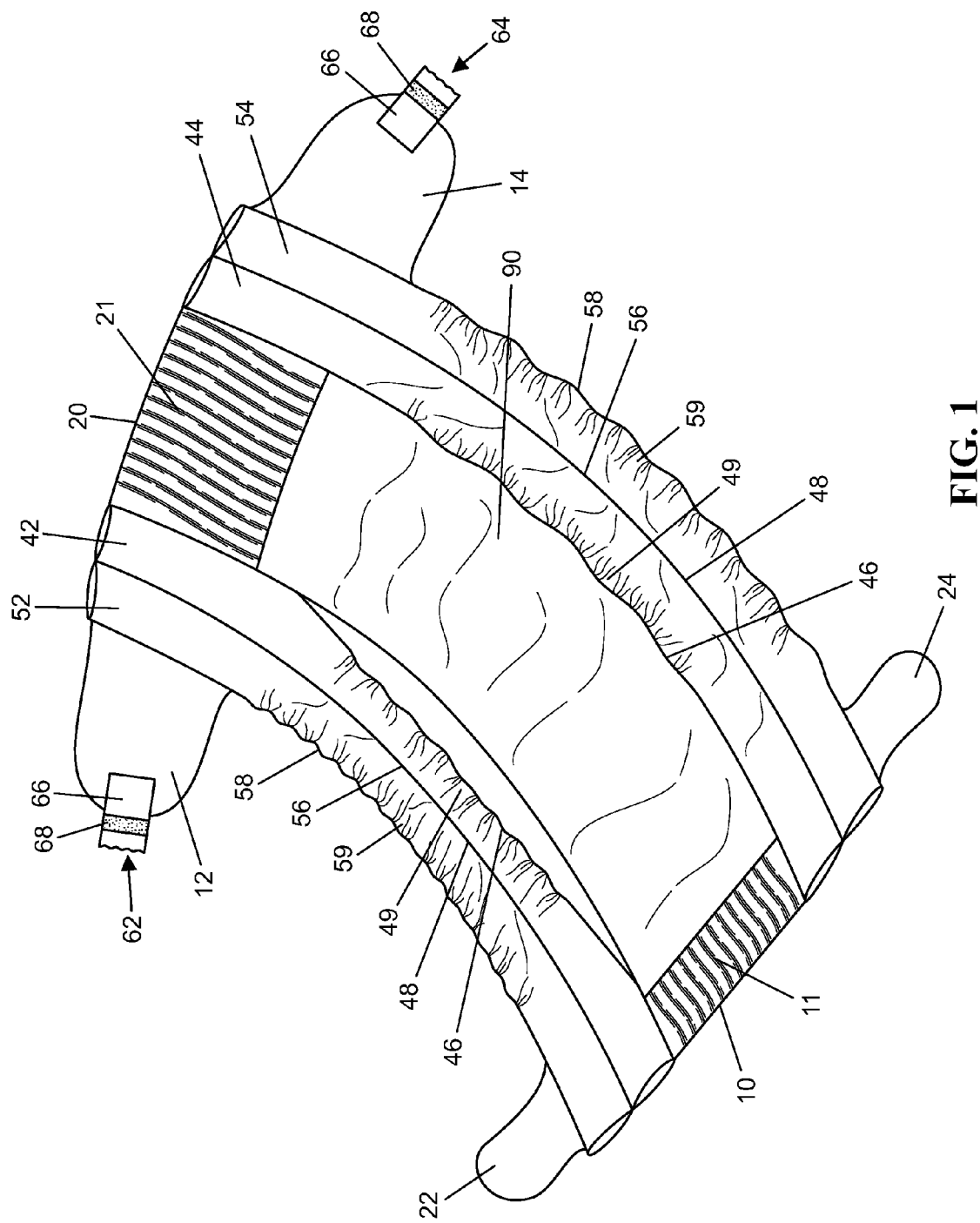
FIG. 1 is a perspective view of an absorbent article according to an example embodiment of the present invention.
Figure 2:
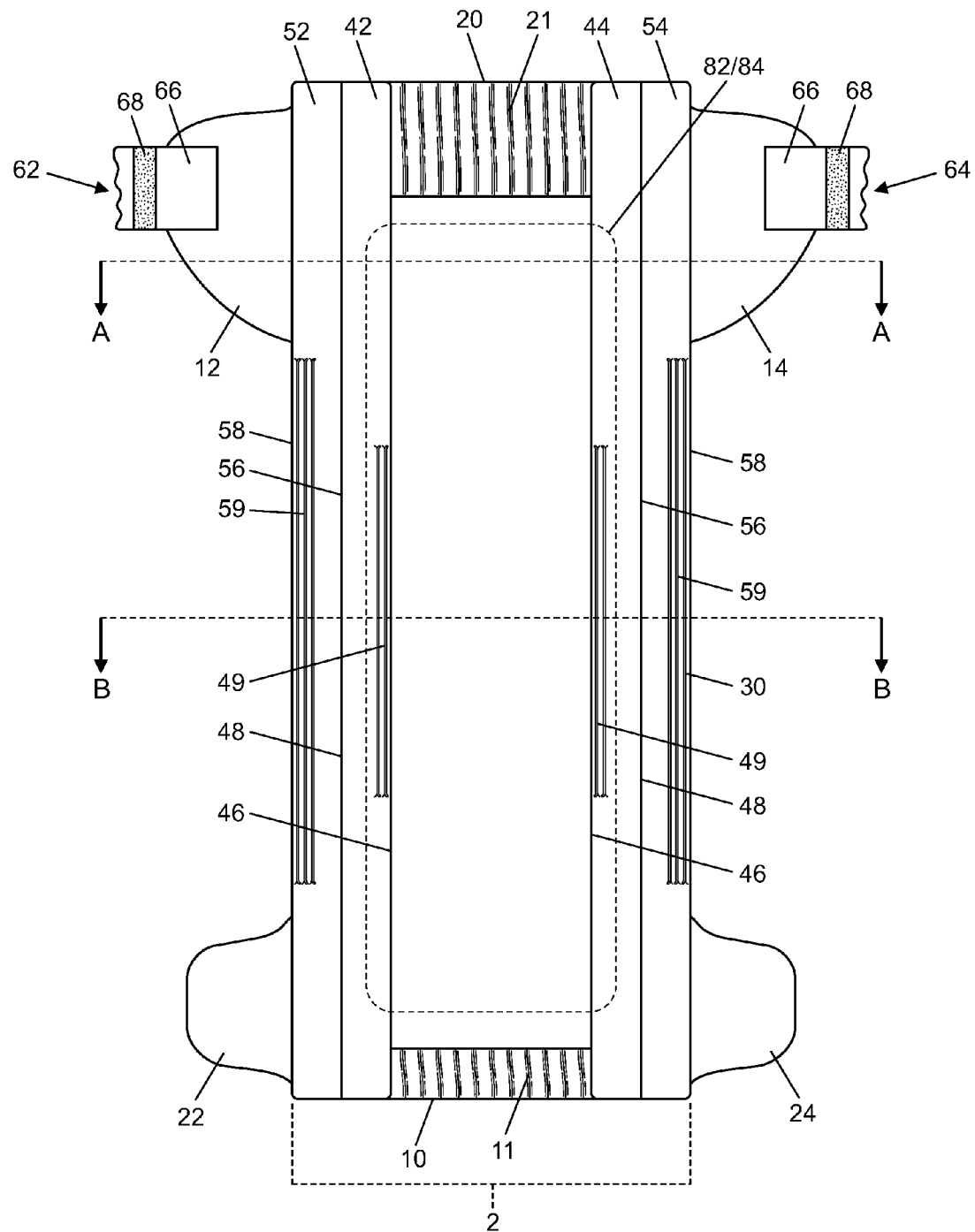
FIG. 2 is a plan view of the inner body facing surface of the absorbent article of FIG. 1.
Figure 3:
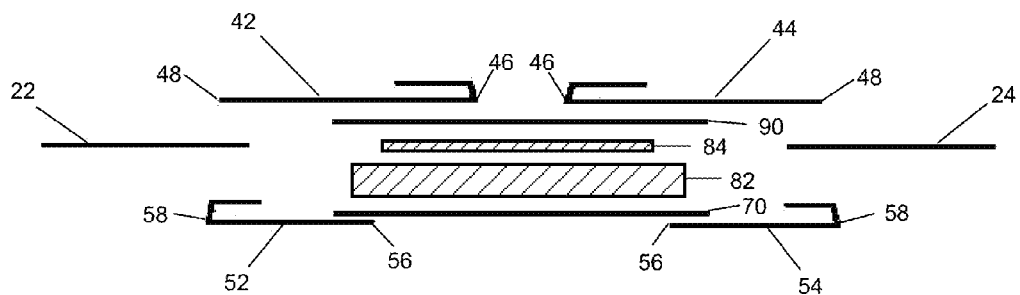
FIG. 3 is a cross-sectional view taken along the line A-A in FIG. 2.
Figure 4:
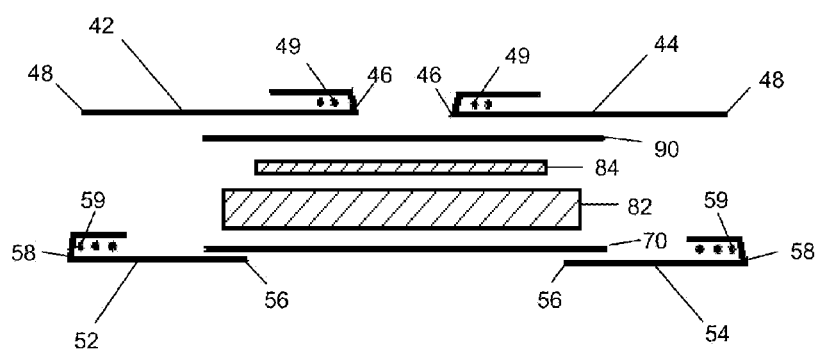
FIG. 4 is a cross-sectional view taken along the line B-B in FIG. 2.

FIGS. 1-2 are perspective and plan views of an absorbent article according to an example embodiment of the present invention, generally designated by reference number 1, in which the inside surface of the absorbent article 1 is facing upwards. FIGS. 3-4 are a cross-sectional views of the absorbent article 1 taken along the line A-A and line B-B of FIG. 2, respectively.

The absorbent article 1 may have a chassis 2 comprising a front waist portion 10, a back waist portion 20, and a crotch portion 30 extending between the front and back waist portions 10, 20. The chassis 2 has longitudinal side edges that generally run in the longitudinal direction (e.g., lengthwise) of the absorbent article 1 and lateral end edges that run between the longitudinal side edges generally in the lateral direction of the absorbent article 1. The chassis 2 may be a layered structure including a backsheet 70, a topsheet 90, an absorbent core 82 disposed between the backsheet 70 and topsheet 90, and an acquisition/distribution layer (ADL) 84 disposed between the absorbent core 82 and the topsheet 90.

The front waist portion 10 may include a front waist elastic 11 and the back waist portion 20 may include a back waist elastic 21. The front and back waist elastics 11, 21 provide elasticity to the waist of the absorbent article 1, so that the absorbent article 1 may have a snug fit around the wearer's waist. As is known in the art, the front and back elastics 11, 21 may be made up of one or more elongated elastic elements extending transversely from the lateral side edges of the front and back waist portion 10, 20. In other embodiments, only the front or back waist portions 10, 20 may include elasticized portions.

A set of inner leg cuffs 42, 44 and a set of outer leg cuffs 52, 54 may extend lengthwise (e.g., longitudinally) from the front waist portion 10 to the back waist portion 20. Outer leg cuffs 52, 54 may be attached to the longitudinal side edges of the chassis 2, for example, to the backsheet 70, topsheet 90 or between the backsheet 70 and topsheet 90. Inner leg cuffs 42, 44 may be disposed on the inside surface of the absorbent article inward of the outer leg cuffs 52, 54, for example, on the inside surface of the outer leg cuffs 52, 54 and/or the topsheet 90. Leg cuffs 42, 44, 52, 44 may be attached by various bonding methods, such as with adhesive, thermal or ultrasonic bonding.

In a preferred embodiment, outer leg cuffs 52, 54 are disposed such that the inner longitudinal side edge 56 is attached to the outside surface of the backsheet 70 and the outer longitudinal side edge 58 is a free edge used as a cuff and which functions, in effect, as the longitudinal side edge of the absorbent article. Inner leg cuffs 42, 44 are disposed such that the proximal edge 48 (e.g., outer longitudinal side edge) is attached to the outer leg cuffs 52, 54 and at least a portion of the distal edge 46 (e.g., the inner longitudinal side edge) is unattached to provide a free edge used as a cuff. The unattached portion of the distal edge 46 may be spaced apart from the body of the absorbent article to form a standing portion of the inner leg cuffs 42, 44. Preferably, the proximal edge 48 of each inner leg cuff 42, 44 is secured adjacent the outer side edge 58 of each of the outer leg cuffs 52, 54 and the distal edge 46 of each of the inner leg cuffs 42, 44 is located inwardly, preferably inward of the longitudinal side edge of the absorbent core 82, so as to substantially cover the entire inside surface of the outer leg cuffs 52, 54 and provide a more tailored appearance.

The inner leg cuffs 42, 44 may be formed from a single piece of material, however the inner leg cuffs 42, 44 may alternatively be comprised of two separate pieces of material, with a first outer piece substantially covering the inside surface of the outer leg cuffs 52, 54 and a second inner piece extending from the first piece to form the standing portion of the inner leg cuffs 42, 44.

Figure 5:
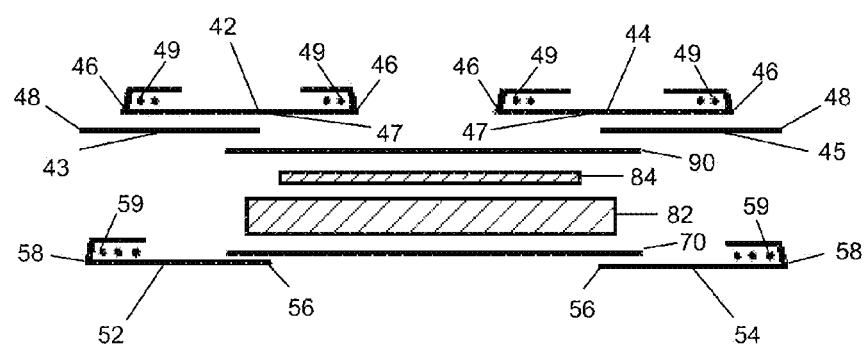
FIG. 5 is a cross-sectional view of the inner leg cuff similar to FIG. 4, but configured as a dual cuff according to another example embodiment of the present invention.

The inner leg cuffs 42, 44 may be formed as single leg cuffs or dual leg cuffs. In a single cuff configuration as shown in FIGS. 1-4, an outer side edge 46 of the inner leg cuff 42, 44 is secured to inside surface of the absorbent article and free, inner side edge 46 is spaced apart from the body of the absorbent article, at least in a region corresponding to the core. In a dual cuff configuration as shown in FIG. 5, an intermediate region 47 of inner leg cuff 42, 44 is secured to the inside surface of the absorbent article such that the inner leg cuff has two standing portions with free, distal side edges 46 that are spaced apart from the body of the absorbent article, at least in a region corresponding to the core. For example, in such a dual cuff configuration, a first outer piece of material 43, 45 may be disposed over the inside surface of the outer leg cuffs 52, 54 with a second inner piece of material attached to the first outer piece to form the two standing portions of the inner leg cuffs 42, 44.

Elastic strands 49, 59 may be disposed along the free, side edges 46, 58 of the inner leg cuff 42, 44 and outer leg cuffs 52, 54 to provide elasticity for forming gathers that provide a tight fit around the wearers crotch and thighs and serve as barrier around to guard against leakage of body exudates. The elastic strands 49, 59 may extend along the entire side edges 46, 58 of the leg cuffs 42, 44, 52, 54 or may extend only along a portion thereof. Preferably, the elastic strands 49, 59 extend at least along a portion of the crotch portion 30. Each leg cuff 42, 44, 52, 54 may contain one or more elastic strands or may use an alternate elastic material such as an elastic film or ribbon. Leg elastics 59 may be configured to tension the outer side edge 58 of the outer leg cuffs 52, 54 to serve as an outer barrier around the wearer's thighs for guarding against leakage of body exudates. Cuff elastics 49 may be configured to tension the distal edge 46 of the inner cuffs 42, 44 to serve as an inner barrier around the wearer's crotch region.

The distal edge 46 of the inner leg cuffs 42, 44 may be tacked down or attached, such as with ultrasonic, adhesive and or thermal bonding, to the outer leg cuff 52, 54 and/or topsheet 90 in areas corresponding to at least the front and back waist portions 10, 20 of the absorbent article. A free portion of the distal edge 46 may remain unattached in an area corresponding to at least a portion of the crotch portion 30. The cuff elastics 49 may extend along at least a portion of the distal edge 46 of the inner leg cuffs 42, 44, and may be configured to lift the free portion of the distal edge 46 of the inner leg cuffs 42, 44 upward and/or inward. In one example embodiment, the cuff elastics 49 extend along the length of the crotch portion 30 but do not extend into the front and back portions 10, 20. In another example embodiment, the cuff elastics 49 extend beyond the crotch portion and into the tacked down portion of the inner cuffs 42, 44. In a dual cuff configuration, the both free, distal edges 48 of the dual cuff may contain cuff elastics 49. The distal edges 46 of the dual cuff may be tacked down or attached to the first outer piece of material 43, 45 in areas corresponding to the front and back waist portions 10, 20 such that portions of the distal edges 46 corresponding to the crotch portion 30 are configured to be lifted to form separate standing cuffs. The more inwardly located distal edge 46 may be biased to extend in an inward direction and the more outwardly located distal edge 46 may be biased to extend in a more outward direction.

The elastic strands 49, 59 may be disposed at various locations on the inner leg cuffs 42, 44 and outer leg cuffs 52, 54 with respect to the longitudinal side edges to provide different aesthetic appearances and fits. In a preferred embodiment, a tailored edge may be formed by locating the elastic strands 49, 59 at the terminal, free, side edges 46, 58 of the inner leg cuffs 42, 44 and/or outer leg cuffs 52, 54, thereby providing a cleaner appearance and a closer fit around the wearer's thighs and crotch area. Preferably, the tailored edge is provided along the entire length of the side edges, however the tailored edge may be provided along only a portion thereof. In another example embodiment, the elastic strands 49, 59 may be located inward of the side edges of the inner leg cuffs 42, 44 and/or outer leg cuffs 52, 54 so as to leave loose material outward of the elastic strands 49, 59.

By way of example, a tailored edge may be formed by attaching the elastic strands 49, 59 on the leg cuffs 42, 44, 52, 54 inward of the side edge 46, 58, with the material of the leg cuff 42, 44, 52, 54 being folded over to enclose the leg elastic strands 49, 59 within a fold along the terminal edge of the leg cuff 42, 44, 52, 54. The folded over material may be secured inward of the elastic strands 49, 59, such as by adhesive, thermal, or ultrasonic bonding. The folded over material may extend along the entire length of the side edges 46, 58 or may extend along only a portion thereof. The elastic strands 49, 59 may be enclosed within the fold along their entire lengths, however the elastic strands 49, 59 may alternatively extend past the folded over material so that only a portion of the elastic strands 49, 59 are enclosed within the fold.

Inner leg cuffs 42, 44 may be made of a substantially or fully liquid impervious material. For example, the inner leg cuffs 42, 44 may be a nonwoven or laminate comprised of one or more webs of polypropylene, polyethylene, polyethylene terephthalate (PET), polylactide (PLA), nylon, polyester and blends of these materials which have been thermally bonded, spunbonded, spunlaced, hydroentangled, or a combination thereof. Preferably, inner leg cuffs 42, 44 are made from a spunbond-meltblown-spunbond ("SMS") laminate. Inner leg cuffs 42, 44 may alternatively be made from a nonwoven that has been treated to make the material substantially liquid impervious. Outer leg cuffs 52, 54 may also be made from a substantially or fully liquid impervious material, such as an SMS or a treated nonwoven, in order to provide protection against leakage. The leg cuffs 42, 44, 52, 54 may be made to vary breathability to air and/or moisture vapor, elasticity, fluid permeability, softness or any other desired characteristic depending on the particular materials and construction used to form the leg cuffs.

In an example embodiment, the leg cuffs 42, 44, 52, 54 may be comprised of a non-elastic material. An example of a suitable material may be a nonwoven having little to no elasticity in the cross direction (CD), e.g., the lateral direction, or in the machine direction (MD), e.g., the longitudinal direction. In this case, any elasticity of the leg cuffs 42, 44, 52, 54 in the longitudinal direction would be due mostly to the elastic strands 49, 59.

In another example embodiment, the leg cuffs 42, 44, 52, 54 may comprised of a material having CD elasticity. In this case, elasticity in the longitudinal direction may be due to the material properties or the elastic strands 49, 59. The CD elasticity of the leg cuff material may provide an improved fit around the wearer's legs and waist. Preferably, the material demonstrates a CD initial force of less than about 200 gm/in at about 50% elongation and a CD initial force of less than about 600 gm/in at about 100% elongation. Examples of a suitable material may be a nonwoven, film, or laminate having CD elasticity. For example, the material may be an elastic nonwoven and film laminate such as Tredegar® FAB-400 sold by Tredegar Corporation of Richmond, Va. or a fluted elastic such as sold by 3M Corp. of St. Paul, Minn.

In an embodiment where inner leg cuffs 42, 44 are formed from more than one piece of material, the pieces of material may be made from of different materials. For example, a first outer piece of the inner leg cuffs 42, 44 substantially covering the inner surface of the outer leg cuffs 52, 44 may be a CD elastic material, while the second inner piece of the inner leg cuffs 42, 44 forming the standing portion of the leg gather may be a non-elastic material.

First and second side back panels 12, 14 may extend outward from the outer longitudinal side edge of the outer leg cuffs 52, 54 at the back waist portion 20. First and second side front panels 22, 24 may extend outward from the outer longitudinal side edge of the outer leg cuffs 52, 54 at the front waist portion 10. The first and second side front panels 22, 24 and first and second side back panels 12, 14 may be formed by attaching material to either one or both of the inner leg cuff 42, 44 and outer leg cuff 52, 54, preferably between the inner leg cuff 42, 44 and outer leg cuff 52, 54. Fastening tabs 62, 64 may be disposed on first and second side back panels 12, 14, and may extend beyond the outer side edge of the first and second side back panels 12, 14.

The first and second side front panels 22, 24 and first and second side back panels 12, 14 may be made of a nonwoven, a film, or a combination thereof. The first and second side front panels 22, 24 and the first and second side back panels 12, 14 may be made to vary breathability to air and/or moisture vapor, elasticity, fluid permeability, softness, or any other desired characteristic depending on the particular materials and construction used to form the side panels. In some example embodiments, the first and second side front panels 22, 24 and the first and second side back panels 12, 14 may be made of a non-elastic or elastic material stretchable in any direction or combination. In some embodiments, only the first and second front panels 22, 24 or the first and second back panels 12, 14 may be elastic, while in other embodiments the first and second side front panels 22, 24 and the first and second side back panels 12, 14 may be elastic.

In an example embodiment in which the absorbent article is in a diaper configuration, the absorbent article 1 may be secured around a wearer's waist by attachment of the fastening tabs 62, 64 of the first and second side back panels 12, 14 to the front waist portion 10. In an example embodiment in which the absorbent article is in a training pant configuration, the absorbent article 1 may be secured around a wearer's waist by attachment of the first side front panel 22 and the second side front panel 24 to the first side back panel 12 and the second side back panel 14, respectively.

The fastening tabs 62, 64 may include a base layer 66 and a fastener element 68. The base layer 66 may be, for example, a nonwoven material layer or a polymeric material layer. The base layer 66 may be attached to the first or second side back panel 12, 14 by any known attachment method, for example, adhesive, ultrasonic bonding, thermal bonding, or the like. Fastener element 68 may be any suitable type of mechanical faster, for example, tapes, adhesives, hook fasteners, loop fasteners, snap fasteners, buttons, or the like. The fastener element 68 may attach to a landing zone or cooperating fastener on the front waist portion 10, or alternatively on the first side front panel 22 or second side front panel 24. For example, in the case of a hook fastener, the landing zone or cooperating fastener may be a strip of loop material or nonwoven material, however the fastener element 68 may also be adapted to engage directly with an outer nonwoven surface of the front waist portion 10 or the first or second side front panels 22, 24, and thus may not require a landing zone or cooperating fastener.

Topsheet 90 may be made of any suitable relatively liquid-pervious material currently known in the art or later discovered that permits passage of a liquid therethrough. The topsheet 90 typically comes in contact with the skin of the wearer, and is preferably made of a material that is gentle to human skin. Examples of suitable topsheet materials include nonwoven, spun-bonded or carded webs of polypropylene, polyethylene, nylon, polyester and blends of these materials, or perforated, apertured or reticulated films, and the like. Nonwoven materials are exemplary because such materials readily allow the passage of liquids to the underlying acquisition/distribution layer 84, and therethrough to absorbent core 82. The topsheet 90 is preferably formed of a single ply of nonwoven material that may be made of fibers comprising polypropylene, polyethylene, polyethylene terephthalate (PET), polylactide (PLA), nylon, polyester and blends of these materials which have been thermally bonded, spun-bonded, spunlaced, hydroentangled, or a combination thereof, or a composite of nonwoven material, such as a spunbond-meltblown-spunbond (SMS) nonwoven. For example, the nonwoven material may have a basis weight of about 8-30 grams per square meter and have appropriate strength and softness for use as a topsheet in an application which will be in contact with human skin. Topsheet 90 may be treated with a surfactant, rendering it hydrophilic to facilitate the passage of moisture through topsheet 90 and into the acquisition/distribution layer 84 and the absorbent core 82. The present invention is not intended to be limited to any particular material for topsheet 90 and other topsheet materials will be readily apparent to those skilled in the art.

Acquisition/distribution layer 84 may be a single layer or multiple layers made of synthetic or natural material, or a combination of both, or a single multilayer apertured film. Acquisition/distribution layer 84 serves to quickly collect and distribute discharged body fluid to absorbent core 82. Because such fluid is typically discharged in gushes, the area of absorbent core 82 proximate to the point of fluid discharge may be overwhelmed by its rate, resulting in a leak. Therefore, the acquisition/distribution layer 84 facilitates transport of the fluid from the point of discharge across its surface area to contact other parts of absorbent core 82 from which it can be more readily absorbed. The use of an acquisition/distribution layer is well known in the art. Accordingly, acquisition/distribution layer 82 of the absorbent article 1 may have any well known or as yet undiscovered construction.

Absorbent core 82 may be any absorbent material which is capable of absorbing and retaining liquids such as urine and certain other body exudates to help prevent the liquid from either rewetting the wearer or otherwise leaking out of the absorbent article. The absorbent material may generally be compressible, conformable to the shape of the wearer's body and should not impede normal movement by the wearer. The absorbent core 82 may be manufactured in a wide variety of sizes and shapes, (e.g., rectangular, hourglass, "T"-shaped, asymmetric, etc.) and from a wide variety of liquid-absorbent materials commonly used in disposable diapers and other absorbent articles Examples of suitable absorbent materials include wood pulp fluff, creped cellulose wadding, melt-blown polymers, chemically stiffened, modified or cross-linked cellulosic fiber, tissue including tissue wraps and tissue laminates, absorbent foams, absorbent sponges, superabsorbent polymers (SAP), absorbent gelling materials, or any similar absorbent material or combinations of materials.

The configuration and construction of absorbent core 82 may also be varied (e.g., the absorbent core may have varying caliper zones, a hydrophilic gradient, an absorbent gelling material gradient, or lower average density and lower average basis weight acquisition zones; or may comprise one or more layers or structures (e.g., sheets or webs). In addition, each layer need not be formed of a single unitary piece of material, but may be formed of a number of smaller strips or components joined together lengthwise or width-wise, as long as they are in fluid communication with one another.) The total absorbent capacity of absorbent core 82 should, however, be compatible with the design loading and the intended use of the absorbent article 1. Further, the size and absorbent capacity of the absorbent core 82 may be varied to accommodate wearers ranging from infants through adults.

Backsheet 70 may be made of a liquid impermeable material or be comprised of multiple layers in which one layer is liquid impermeable. For example, the backsheet 70 may be comprised of an inner layer of film that is suitably pliable and liquid impervious and an outer layer of a liquid and/or vapor-pervious material. Typical materials for the inner layer of the backsheet 70 include films of polyethylene, polypropylene, polyester, nylon and polyvinyl chloride (PVC) and blends of these materials. For example, the inner layer may be made of a polyethylene film having a thickness in the range of about 0.4 to 2.0 mils. Other inner layer materials may be readily apparent to those skilled in the art. Inner layer of backsheet 70 preferably has sufficient liquid imperviousness to prevent any leakage of fluids. The outer layer of the backsheet 70 may be made of a liquid and/or vapor-pervious material which may be selected from the same group of materials from which the topsheet was selected. The outer layer may have a basis weight of, for example, between about 5-45 grams per square meter. Unlike topsheet 90, however, the material used for the outer layer of the backsheet 70 is preferably rendered hydrophobic by omitting the surfactant discussed above with respect to topsheet 90. The outer layer of the backsheet 70 may be manufactured by well known methods such as thermal bonding, chemical bonding, spun bonding and hydroentanglement, or by a combination of spun bonding and hydroentanglement.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article having an inside surface that faces a wearer's body when the absorbent article is worn, and an outside surface opposite the inside surface, the absorbent article comprising:
   a chassis having a front waist portion, a back waist portion, and crotch portion extending between the front and back waist portions, the chassis having longitudinal side edges and lateral side edges, the chassis comprising:
      a liquid pervious topsheet,
      a backsheet, at least a portion of the backsheet being liquid impervious, and
      an absorbent core disposed between the topsheet and the backsheet;
   an outer leg cuff disposed outward of each of the longitudinal side edges of the chassis, each of the outer leg cuffs having an inner longitudinal side edge attached along at least a portion of one of the longitudinal sides of the chassis and an outer longitudinal side edge having elastics forming a gather along at least a portion thereof;
   one or more inner leg cuffs disposed on the inside surface of the chassis along each of the longitudinal side edges thereof, each of the inner leg cuffs having a proximal longitudinal side edge directly attached to and along the outer longitudinal side edge of one of the outer leg cuffs and a distal longitudinal side edge having elastics forming a gather along at least a portion of the crotch portion, each inner leg cuff being separate from the topsheet and backsheet between the proximal and distal longitudinal side edges so that each inner leg cuff is attached to the absorbent article along the at least a portion of the crotch portion only by virtue of its attachment to a corresponding outer leg cuff; and
   one or more fastening components disposed at the outer longitudinal side of the outer leg cuffs which are adapted to fasten the absorbent article around the waist of the wearer.

2. The absorbent article of claim 1, wherein at least a portion of the distal longitudinal side edge of each of the inner leg cuffs is unattached so as to be spaced apart from the inside surface of the chassis.

3. The absorbent article of claim 1, wherein each of the inner leg cuffs are attached to at least one of the outer leg cuff and the topsheet moving inward from the proximal longitudinal side edge toward the distal longitudinal side edge of the inner leg cuff.

4. The absorbent article of claim 1, wherein each of the inner leg cuffs are attached at the distal longitudinal side edge thereof to at least one of the outer leg cuff and the topsheet adjacent at least one of the front and back waist portions.

5. The absorbent article of claim 1, wherein the elastics are disposed adjacent the terminal, longitudinal side edge of the outer leg cuffs.

6. The absorbent article of claim 5, wherein a portion of the outer leg cuffs is disposed outward of the elastics and is folded over to enclose the elastics within a fold of the leg cuffs along terminal, longitudinal side edges thereof.

7. The absorbent article of claim 1, wherein the outer leg cuffs are joined to the chassis by attachment to topsheet, the backsheet, or between the topsheet and backsheet.

8. The absorbent article of claim 1, wherein at least one of the inner and outer leg cuffs are comprised of at least one of a nonwoven, a film, and a laminate thereof.

9. The absorbent article of claim 1, wherein at least one of the inner and outer leg cuffs are comprised of a material that is breathable to at least one of air and moisture vapor.

10. The absorbent article of claim 1, wherein at least one of the inner and outer leg cuffs are comprised of a material which is substantially non-elastic.

11. The absorbent article of claim 1, wherein at least one of the inner and outer leg cuffs are comprised of a material which is substantially elastic in the cross-direction (CD).

12. The absorbent article of claim 1, wherein the fastening components comprise:
   a first side back panel and a second side back panel extending outward from the outer leg cuffs adjacent the back waist portion; and
   a fastener disposed at each of the first side back panel and second side back panel adapted for attachment to the front waist portion of the chassis.

13. The absorbent article of claim 12, wherein the first and second side back panels are attached between the outer leg cuff and the inner leg cuff.

14. The absorbent article of claim 12, wherein the first and second back side panels are comprised of at least one of a nonwoven, a film, and a laminate thereof.

15. The absorbent article of claim 12, wherein the first and second back side panels are comprised of a substantially non-elastic material.

16. The absorbent article of claim 12, wherein the first and second back side panels are comprised of a substantially elastic material.

17. The absorbent article of claim 12, wherein the fasteners are adapted for attachment to the outer surface of the front waist portion of the chassis.

18. The absorbent article of claim 12, wherein the fasteners are adapted for attachment to landing zones on the outer surface of the front waist portion of the chassis.

19. The absorbent article of claim 12, further comprising:
   a first side front panel and a second side front panel extending outward from the outer leg cuffs adjacent the front waist portion.

20. The absorbent article of claim 19, wherein the first and second side front panels are attached between the outer leg cuff and the inner leg cuff.

21. The absorbent article of claim 19, wherein the fasteners are adapted for attachment to the outer surface of the front side panels.

22. The absorbent article of claim 1, wherein the topsheet is comprised of a nonwoven material.

23. The absorbent article of claim 1, wherein the backsheet is comprised of a film, a nonwoven, or a laminate thereof.

* * * * *